US008720441B2

(12) United States Patent
Sinderby (10) Patent No.: US 8,720,441 B2
(45) Date of Patent: May 13, 2014

(54) DETERMINING PATIENT-VENTILATOR BREATH CONTRIBUTION INDEX IN SPONTANEOUSLY BREATHING, MECHANICALLY VENTILATED PATIENTS

(75) Inventor: Christer Sinderby, Toronto (CA)

(73) Assignee: St. Michael's Hospital, Toronto, Ontario (CA)

( * ) Notice: Subject to any disclaimer, the term of this patent is extended or adjusted under 35 U.S.C. 154(b) by 250 days.

(21) Appl. No.: 13/059,545

(22) PCT Filed: Aug. 26, 2009

(86) PCT No.: PCT/CA2009/001194
§ 371 (c)(1),
(2), (4) Date: May 6, 2011

(87) PCT Pub. No.: WO2010/022513
PCT Pub. Date: Mar. 4, 2010

(65) Prior Publication Data
US 2012/0103334 A1 May 3, 2012

Related U.S. Application Data

(60) Provisional application No. 61/136,343, filed on Aug. 28, 2008.

(51) Int. Cl.
*A61B 5/08* (2006.01)
*A61M 16/00* (2006.01)
(52) U.S. Cl.
USPC .............. 128/204.23; 128/204.21; 600/529; 600/536; 600/546
(58) Field of Classification Search
CPC .............. A61B 5/0488; A61B 5/08; A61M 2016/0021; A61M 2016/0018

USPC ......... 128/204.18, 204.21, 204.23, 204.26, 2; 600/546–547
See application file for complete search history.

(56) References Cited

U.S. PATENT DOCUMENTS

| 5,107,830 A | 4/1992 | Younes |
| 5,671,752 A | 9/1997 | Sinderby et al. |

(Continued)

FOREIGN PATENT DOCUMENTS

| CA | 2 230 857 | 8/1999 |
| CA | 2 379 671 | 2/2001 |
| CA | 2 519 041 | 9/2004 |
| WO | WO 2005077268 A1 * | 8/2005 |

OTHER PUBLICATIONS

Beck, et al, Electrical Activity of the Diaphragm During Pressure Support Ventilation in Acute Respiratory Failure, 2001, Am J Respir Crit Care Med, vol. 164, pp. 419-424.*

(Continued)

*Primary Examiner* — Justine Yu
*Assistant Examiner* — Timothy Stanis
(74) *Attorney, Agent, or Firm* — Fay Kaplun & Marcin, LLP (57) ABSTRACT

The present invention relates to a system and method for determining a patient-ventilator breath contribution index in a spontaneously breathing, mechanically ventilated patient. A patient's efficiency to generate an inspiratory volume without mechanical ventilatory assist and a patient's efficiency to generate an inspiratory volume with mechanical ventilatory assist are calculated and used to determine the patient-ventilator breath contribution index.

14 Claims, 4 Drawing Sheets

(56) References Cited

U.S. PATENT DOCUMENTS

| | | | |
|---|---|---|---|
| 5,820,560 A | 10/1998 | Sinderby et al. | |
| 5,884,622 A | 3/1999 | Younes | |
| 6,679,258 B1* | 1/2004 | Strom | 128/204.21 |
| 2003/0188748 A1* | 10/2003 | Sinderby et al. | 128/204.21 |
| 2006/0070624 A1* | 4/2006 | Kane et al. | 128/204.23 |
| 2007/0062533 A1 | 3/2007 | Choncholas et al. | |
| 2008/0234595 A1 | 9/2008 | Ranieri et al. | |

OTHER PUBLICATIONS

Finucane, et al, Efficiency of the Normal Human Diaphragm with Hyperinflation, 2005, J Appl Physiol, vol. 99, pp. 1402-1411.*

* cited by examiner

Figure shows the PVBC index (Y-axis) and relative reduction in esophageal inspiratory pressure swings (%) (X-axis) in nine rabbits.

FIG. 3

Figure shows flow, volume airway pressure and EAdi for assisted breaths (all but breath #4) and non-assisted breath (#4). In this case the ratio of Vt and EAdi for breath # 4 and divided by the ratio of Vt and EAdi for breath #3 could be used to calculate the PVBC index.

FIG. 4

DETERMINING PATIENT-VENTILATOR BREATH CONTRIBUTION INDEX IN SPONTANEOUSLY BREATHING, MECHANICALLY VENTILATED PATIENTS

FIELD

The present invention generally relates to mechanical ventilation in spontaneously breathing patients. More specifically, the present invention is concerned with a system and method for determining a patient-ventilator breath contribution index in a spontaneously breathing, mechanically ventilated patient.

BACKGROUND

Mechanical ventilation can be applied to a spontaneously breathing patient, for example through a mechanical ventilator. Then, the function of the mechanical ventilatory assist is to help the patient to maintain adequate ventilation by assisting the patient's weak respiratory muscles and by sharing the inspiratory load between the patient and the mechanical ventilator. When the mechanical ventilatory assist, expressed in terms of pressure, flow and/or volume, is delivered in synchrony with the patient's inspiratory effort, meaning that the mechanical ventilatory assist is delivered to the patient simultaneously with patient's inspiration, the mechanical ventilator will partially or completely overcome the inspiratory flow resistive and elastic loads induced by the respiratory system formed by the patient's lungs and thorax.

Furthermore, when the mechanical ventilator is neurally controlled as proposed in U.S. Pat. No. 5,820,560 granted to Sinderby et al on Oct. 13, 1998, the mechanical ventilatory assist can be delivered at the neural onset of the patient's inspiration so as to partially or completely overcome the inspiratory threshold load caused by the dynamic hyperinflation, also referred to as the intrinsic positive end-expiratory pressure (PEEP).

The currently used mechanical ventilators present a major limitation since they are unable to adequately determine the level of unloading of the patient's respiratory muscles or the patient's contribution to the inspiration when both mechanical ventilatory assist and the patient's own inspiratory muscles contribute to the inspiration. Even though methods for predicting unloading of the patient's respiratory muscles and the resistive and elastic load caused by the patient's respiratory system have been proposed, they still present the drawbacks of failing to show the patient's neural effort and neglecting the effect of the patient's muscle weakness and intrinsic PEEP.

Accordingly, there is a need for a system and method for determining a patient-ventilator breath contribution index in a spontaneously breathing, mechanically ventilated patient.

DETAILED DESCRIPTION

In accordance with a first aspect of the present invention, there is provided a method for determining a patient-ventilator breath contribution index in a spontaneously breathing, mechanically ventilated patient, comprising: calculating a patient's efficiency to generate an inspiratory volume without mechanical ventilatory assist; calculating a patient's efficiency to generate an inspiratory volume with mechanical ventilatory assist; and calculating the patient-ventilator breath contribution index using the calculated patient's efficiency to generate an inspiratory volume without mechanical ventilatory assist and the calculated patient's efficiency to generate an inspiratory volume with mechanical ventilatory assist.

In accordance with another aspect of the present invention, there is provided a system for determining a patient-ventilator breath contribution index in a spontaneously breathing, mechanically ventilated patient, comprising: a first calculator of a patient's efficiency to generate an inspiratory volume without mechanical ventilatory assist; a second calculator of a patient's efficiency to generate an inspiratory volume with mechanical ventilatory assist; and a third calculator of the patient-ventilator breath contribution index using the calculated patient's efficiency to generate an inspiratory volume without mechanical ventilatory assist and the calculated patient's efficiency to generate an inspiratory volume with mechanical ventilatory assist.

The foregoing and other objects, advantages and features of the present invention will become more apparent upon reading of the following non-restrictive description of illustrative embodiments thereof, given by way of example only with reference to the accompanying drawings.

The illustrative embodiments presented in the following non-restrictive description relate to a system and method for determining a patient-ventilator breath contribution (PVBC) index in a spontaneously breathing, mechanically ventilated patient.

Generally stated, the method for determining the patient-ventilator breath contribution (PVBC) index in a spontaneously breathing, mechanically ventilated patient is based on a relation between the patient's efficiency to generate an inspiratory volume without mechanical ventilatory assist and the patient's efficiency to generate an inspiratory volume with mechanical ventilatory assist.

More specifically, the method for determining the patient-ventilator breath contribution (PVBC) index in a spontaneously breathing, mechanically ventilated patient is based on measurements of (a) the electrical activity of a patient's respiratory muscle during inspiration, for example the patient's diaphragm, and (b) the patient's inspiratory volume, for example the tidal inspiratory volume (Vt).

The electrical activity (EAdi) represents a spatiotemporal recruitment of the patient's diaphragm. Therefore, the level of electrical activity of the patient's diaphragm (EAdi) varies, more specifically increases and decreases with respiratory loads, including the inspiratory flow resistive and/or elastic loads induced by the patient's respiratory system and/or by an external load such as an extrapulmonary load source. Also, when any of the patient's respiratory muscles weakens, the ability of the patient's respiratory muscle to generate a certain force/pressure in response to a given activation reduces and, accordingly, the level of patient's diaphragm electrical activity (EAdi) required for generating this certain force/pressure increases. This increase of the level of the patient's diaphragm electrical activity (EAdi) is indicative of the level of activation of the diaphragm required to overcome the respiratory loads, including the inspiratory flow resistive and/or elastic loads, the inspiratory threshold or intrinsic PEEP load and any respiratory muscle weakness. Moreover, this increase in diaphragm electrical activity (EAdi) can be used for determining the effects of a patient's chest wall restriction, a patient's reduced abdominal compliance, and other external loads that reduce the efficiency of lung distension.

The dynamics in different situations between the diaphragm electrical activity (EAdi) during inspiration and the inspiratory volume (Vt) have shown that an increased respiratory load, whether resistive and/or elastic, for a given inspiratory volume (Vt) causes the diaphragm electrical activity (EAdi) during inspiration to increase if no ventilatory assist is supplied to the patient. However, if ventilatory assist is supplied to the patient by a mechanical ventilator, then either the inspiratory volume (Vt) increases or the diaphragm electrical activity (EAdi) during inspiration decreases.

When no ventilatory assist is supplied to the patient, an increased weakness of a patient's respiratory muscle causes the diaphragm electrical activity (EAdi) during inspiration to increase in order to maintain a given inspiratory volume (Vt), i.e. the patient's efficiency to generate an inspiratory volume is decreased. When ventilatory assist is supplied to the patient by a mechanical ventilator, then either the inspiratory volume (Vt) increases or the diaphragm electrical activity (EAdi) during inspiration decreases, i.e. the patient's efficiency to generate an inspiratory volume is increased.

In another example, increase of the intrinsic PEEP caused, for example, by dynamic hyperinflation can cause the patient's respiratory muscles, including the diaphragm to become weaker. This is due to the fact that the chest wall configuration is altered upon hyperinflation. Also, increase of the intrinsic PEEP can act as a threshold load and cause the diaphragm electrical activity (EAdi) during inspiration to increase in order to maintain a given inspiratory volume (Vt) when no ventilatory assist is supplied to the patient. When ventilatory assist is supplied, at the onset of neural inspiratory effort (overcoming intrinsic PEEP), to the patient by a mechanical ventilator, either the inspiratory volume (Vt) increases or the diaphragm electrical activity (EAdi) during inspiration decreases.

The ratio between the inspiratory volume (Vt) and the diaphragm electrical activity (EAdi) during inspiration can be used for expressing the efficiency of the patient's inspiration. More specifically, $Vt/EAdi_{assist}$ expresses the patient's inspiration efficiency with mechanical ventilatory assist and $Vt/EAdi_{no\text{-}assist}$ expresses the patient's inspiration efficiency without mechanical ventilatory assist. Then, the ratio between $Vt/EAdi_{no\text{-}assist}$ and $Vt/EAdi_{assist}$ describes and expresses the patient's contribution to a breath during mechanical ventilatory assist. In the following description, this ratio will be referred to as the patient-ventilator breath contribution (PVBC) index.

During breathing, the inspiratory volume (Vt) generated by the patient depends on the efficiency of the transformation of a neural activation of his/her respiratory centers to the respiratory muscles and the load imposed by the respiratory system. Indeed, activating the respiratory muscles causes the lungs of the patient to expand and thus to generate an inspiratory flow and volume. This efficiency of the above-defined transformation is referred to as the so called neuroventilatory efficiency.

Figure 1:
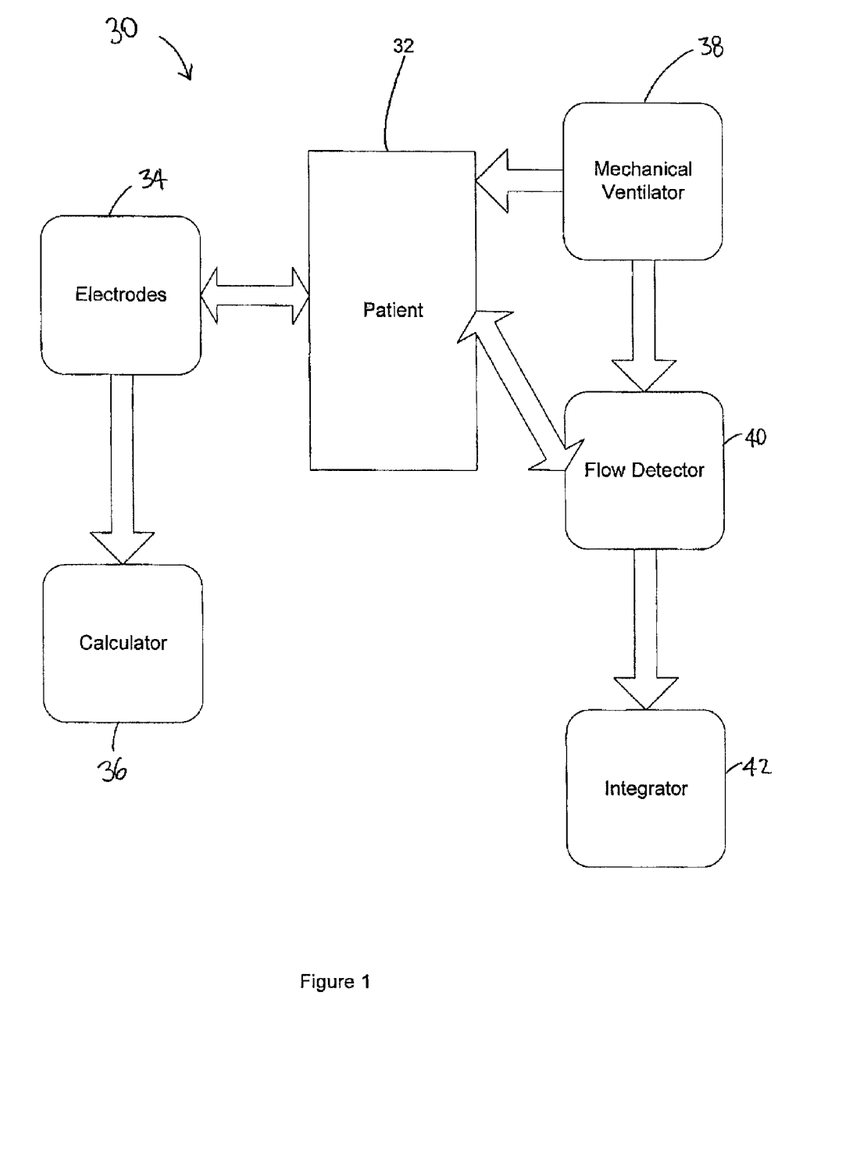
FIG. 1 is a schematic block diagram of a system for determining a patient-ventilator breath contribution (PVBC) index in a spontaneously breathing, mechanically ventilated patient.

Turning now to FIG. 1, a system 30 for measuring the diaphragm electrical activity (EAdi) during inspiration and the inspiratory volume (Vt) in a patient 32 will be described.

Measurement of the Diaphragm Electrical Activity (EAdi)

The electrical activity of the patient's diaphragm (EAdi) during inspiration is measured by an EAdi detector comprising an array of electrodes 34 for example mounted on a free end section of an oesophageal catheter (not shown). The oesophageal catheter including the array of electrodes 34 can be introduced in the patient 32 through one nostril or the mouth and then through the oesophagus until the array of electrodes 34 reaches the level of the patient's diaphragm. The array of electrodes 34, thus positioned, senses EAdi signals generated by the patient's diaphragm during breathing of the patient 32. The sensed EAdi signals are then processed through a calculator 36 of the EAdi detector connected to the array of electrodes 34 to produce and supply a measured electrical activity of the patient's diaphragm (EAdi). An example of configuration of the array of electrodes mounted on a free end section of an esophageal catheter as well as an example of processing of the EAdi signals detected through the array of electrodes is described in U.S. Pat. No. 5,671,752 granted to Sinderby et al on Sep. 30, 1997 of which the contents is hereby incorporated by reference.

Measurement of the Inspiratory Volume (Vt)

Measurement of the patient's inspiratory volume (Vt) can be done, for example, by a volume detector through integration of the patient's inspiratory flow which can be measured through a flow detector connected a mechanical ventilator supplying ventilatory assist to the patient. Of course, it is within the scope of the present invention to use other available and suitable methods for measuring the patient's inspiratory volume (Vt).

More specifically, referring to FIG. 1, the patient 32 can wear an inspiratory implement or mask (not shown) connected to a mechanical ventilator 38 for providing ventilatory assist to the patient 32. Also connected to the mechanical ventilator 38 and the patient 32 is a flow detector 40 of the volume detector for sensing an inspiratory flow in the respiratory circuit of the patient 32.

The detected inspiratory flow is then processed through an integrator 42 of the volume detector connected to the flow detector 40. The function of the integrator 42 is to integrate the inspiratory flow detected by the flow detector 40 into a volume such as the above mentioned tidal inspiratory volume (Vt).

Detecting inspiratory flow and integrating the detected inspiratory flow to obtain the tidal inspiratory volume (Vt) are believed to be otherwise within the ability of those of ordinary skill in the art and accordingly will not be further described in the present specification.

Determination of the Patient-Ventilator Breath Contribution (PVBC) Index

A method 50 for determining the patient-ventilator breath contribution (PVBC) index will now be described with reference to both FIGS. 1 and 2.

Operation 52

In operation 52 (FIG. 2), a breathing mode is selected between a ventilatory assist mode 54 and a no-ventilatory assist mode 66. For that purpose, the mechanical ventilator 38

(FIG. 1) can be programmed to either generate no pressure, flow and/or volume assist (no-ventilatory assist) or to generate a pressure, flow and/or volume assist at a certain higher level adequate to assist the patient's breathing efforts. If positive end-expiratory pressure (PEEP) is applied, no-ventilatory assist can also constitute the level of the PEEP.

Figure 2:
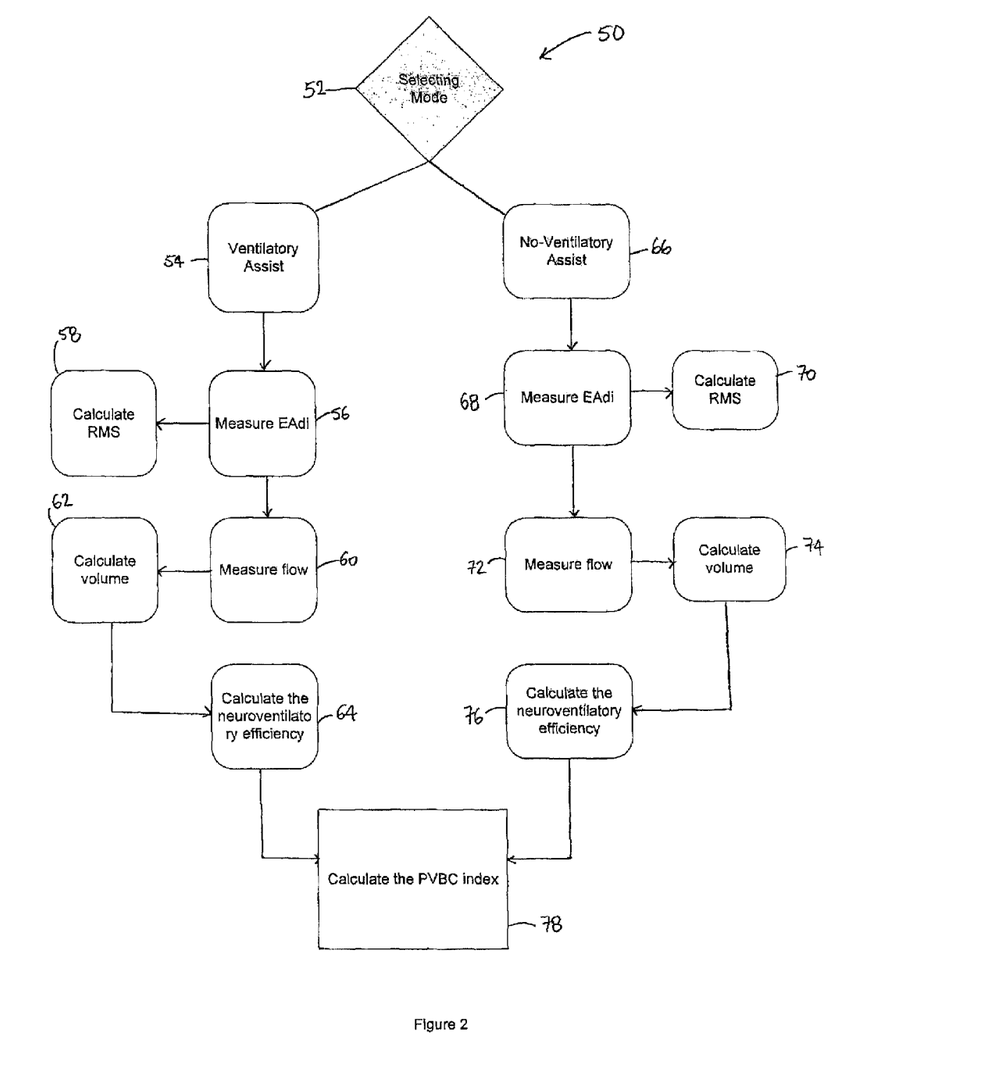
FIG. 2 is a flow chart of a method for determining the patient-ventilator breath contribution (PVBC) index in a spontaneously breathing, mechanically ventilated patient.

Operation 52 (FIG. 2) normally selects the ventilatory assist mode 54 (FIG. 2). Then, the mechanical ventilator 38 (FIG. 1) delivers a ventilatory assist to the patient 32 during patient's inspiration. For example, ventilatory assist can be delivered to the patient 32 (FIG. 1) during the period when the diaphragm electrical activity (EAdi) during inspiration is present and in proportion to the diaphragm electrical activity (EAdi) as disclosed in U.S. Pat. No. 5,820,560, granted to Sinderby et al on Oct. 13, 1998.

Operation 56

In operation 56 (FIG. 2), the diaphragm electrical activity (EAdi) during inspiration (corresponding to one breath of the patient) and without mechanical ventilatory assist is measured through the array of electrodes 34 and calculator 36 (FIG. 1) using the above described technique. For example, the technique of double subtraction as disclosed in the above mentioned U.S. Pat. No. 5,671,752 granted to Sinderby et al on Sep. 30, 1997 can be used to produce an improved measure of the patient's diaphragm electrical activity (EAdi).

Operation 58

In operation 58 (FIG. 2), the RMS (Root Mean Square) of the measured diaphragm electrical activity (EAdi) during inspiration is calculated, for example through the calculator 36 (FIG. 1). As a non-limitative example, the RMS value of the measured diaphragm electrical activity (EAdi) can be expressed in $\mu V$.

A method for determining neural activation of the respiratory centers of the patient 32 (FIG. 1) and supplied to the inspiratory muscles is, for example, to measure the electrical activity of the respiratory muscles during inspiration, for example the patient's diaphragm using the array of electrodes 34 introduced in the esophagus of the patient 32 as proposed in the above mentioned U.S. Pat. No. 5,671,752 granted to Sinderby et al on Sep. 30, 1997. However, it is within the scope of the present invention to obtain, beside the diaphragm electrical activity (EAdi), other types of measures representative of the neural activation or inspiratory effort. Also, all of these measures, including the diaphragm electrical activity (EAdi), can be expressed in terms of mean, peak, etc., values of signals.

Operation 60

In operation 60 (FIG. 2), the inspiratory flow in the patient's respiratory circuit (corresponding to said one breath of the patient with mechanical respiratory assist) is detected using, for example, the flow detector 40 (FIG. 1). The flow detector 40 can be an integral part of the mechanical ventilator 38 (FIG. 1) or it can be an equipment added to the mechanical ventilator 38.

Operation 62

In operation 62 (FIG. 2), the detected inspiratory flow from the flow detector 40 (FIG. 1) is integrated to produce the inspiratory volume (Vt). For example, the integrator 42 (FIG. 1) can be used to proceed with this integration of the inspiratory flow. The calculated inspiratory volume (Vt) can be, for example, expressed in mL.

Operation 64

In operation 64 (FIG. 2), the inspiratory volume (Vt) calculated in operation 62 is expressed in relation to, for example, the RMS value of the diaphragm electrical activity (EAdi) during inspiration calculated in operation 58, or in relation to any other measures reflecting the neural inspiratory effort. More specifically, at the end of each inspiration, a calculator determines the patient's efficiency to generate an inspiratory volume with mechanical ventilatory assist using the relation $Vt/EAdi_{assist}$ that can be expressed, for example, in $mL/\mu V$. This patient's efficiency to generate an inspiratory volume with mechanical ventilatory assist describes a neuroventilatory efficiency index during assisted inspiration.

Periodically, each time during one breath of the patient, operation 52 selects the no-ventilatory assist mode 66 (FIG. 2). The mechanical ventilator 38 then reduces the pressure, flow, and/or volume assist to a zero level or to the level of the positive end-expiratory pressure (PEEP). In situations where ventilatory assist cannot be entirely removed, it is within the scope of the method according to the invention to reduce the pressure, flow, and/or volume assist to a level higher than the zero level or PEEP level and use a linear or non-linear prediction model to estimate what the reduction in diaphragm electrical activity (EAdi) and inspiratory volume (Vt) would have been at the zero level or PEEP level.

Operation 68

In operation 68 (FIG. 2), the diaphragm electrical activity (EAdi) during inspiration (corresponding to said one breath of the patient without mechanical respiratory assist) or other measure of neural inspiratory effort is measured in the same manner as in operation 56 (FIG. 2), but without ventilatory assist to the patient's inspiration.

Operation 70

In operation 70, the measured diaphragm electrical activity (EAdi) during inspiration from operation 68 is then processed through the calculator 36 (FIG. 1) to produce a RMS value of the measured diaphragm electrical activity (EAdi), expressed for example in $\mu V$. As indicated in the foregoing description, other values such as mean, peak, etc., values of the measured diaphragm electrical activity (EAdi) or other measure reflecting neural inspiratory effort of the patient 32 can be calculated.

Operation 72

In operation 72 (FIG. 2), the inspiratory flow (corresponding to said one breath of the patient without mechanical respiratory assist) is measured in the same manner as in operation 60, but without ventilatory assist.

Operation 74

Then, in operation 74, the inspiratory volume (Vt) (corresponding to said one breath of the patient without mechanical respiratory assist) is calculated by integrating the inspiratory flow measured in operation 72 in the same manner as in operation 62. The calculated inspiratory volume (Vt) can be expressed, for example, in mL.

Operation 76

Next, in operation 76 (FIG. 2), the inspiratory volume (Vt) is expressed in relation to the RMS value of the measured diaphragm electrical activity (EAdi) during inspiration calculated in operation 70, or as mentioned above any other measures reflecting the neural inspiratory effort of the patient 32 without ventilatory assist. More specifically, at the end of each inspiration, the patient's efficiency to generate an inspiratory volume without mechanical ventilatory assist is calculated using the relation $Vt/EAdi_{no-assist}$ and is expressed, for example, in $mL/\mu V$. This patient's efficiency to generate an inspiratory volume without mechanical ventilatory assist describes the neuroventilatory efficiency index without ventilatory assist. In order to avoid influences of non-linearity, it is possible to calculate the ratio of $Vt/EAdi_{no-assist}$ and $Vt/EAdi_{assist}$ at matching EAdi levels. In other words, one could calculate the ratio between $Vt_{no-assist}$ and $Vt_{assist}$ at the same EAdi levels by only integrating volume until a given EAdi level.

It should be noted that the two (2) modes 54 and 66 (with and without ventilatory assist) can be used in succession with no particular or predetermined period. For example, the ventilatory assist mode 54 can be used first during a predetermined number of breaths, followed by the no-ventilatory assist mode 66 during one breath and this scheme is continued as long as it is desired or required (see for example FIG. 4 in which the Pmo curve shows a succession of ventilator-assisted breaths interrupted by one non-assisted breath.

Operation 78

Having obtained the measure of the patient's efficiency to generate an inspiratory volume without mechanical ventilatory assist in operation 76 during a given breath (for example breath No. 4 of FIG. 4) and the measure of the patient's efficiency to generate an inspiratory volume with mechanical ventilatory assist in operation 64 during a following or preceding breath (for example breath No. 3 in FIG. 4), a calculator then calculates the patient-ventilator breath contribution (PVBC) index in operation 78 for the patient 32 (FIG. 1). More specifically, the patient-ventilator breath contribution (PVBC) index is calculated using the following relation:

$$PVBC = \frac{Vt/EAdi_{no\text{-}assist}}{Vt/EAdi_{assist}} \quad (1)$$

As described in the foregoing description, the patient-ventilator breath contribution (PVBC) index describes the patient's contribution to a breath during patient's mechanical ventilatory assist. The patient-ventilator breath contribution (PVBC) index is obtained in relative units expressing the ratio of the patient's efficiency to generate an inspiratory volume without mechanical ventilatory assist to the patient's efficiency to generate an inspiratory volume with mechanical ventilatory assist. As can be appreciated, the patient-ventilator breath contribution (PVBC) index is linked to the relative unloading of the patient's inspiratory muscles, including in particular the diaphragm.

In order to experimentally verify the patient-ventilator breath contribution (PVBC) index calculated as described above, the real relative unloading of the respiratory muscles of patients was measured as the relative reduction, in percentage (%), of the inspiratory esophageal pressure swings (Pes). The neural drive was measured as the diaphragm electrical activity (EAdi) during inspiration. The experimentation started from a condition of no-ventilatory assist applied to the patients and continued with a condition of incrementally increasing ventilatory assist to the patients using, for example, neurally adjusted ventilatory assist (NAVA) as disclosed in U.S. Pat. No. 5,820,560, granted to Sinderby et al on Oct. 13, 1998.

Figure 3:
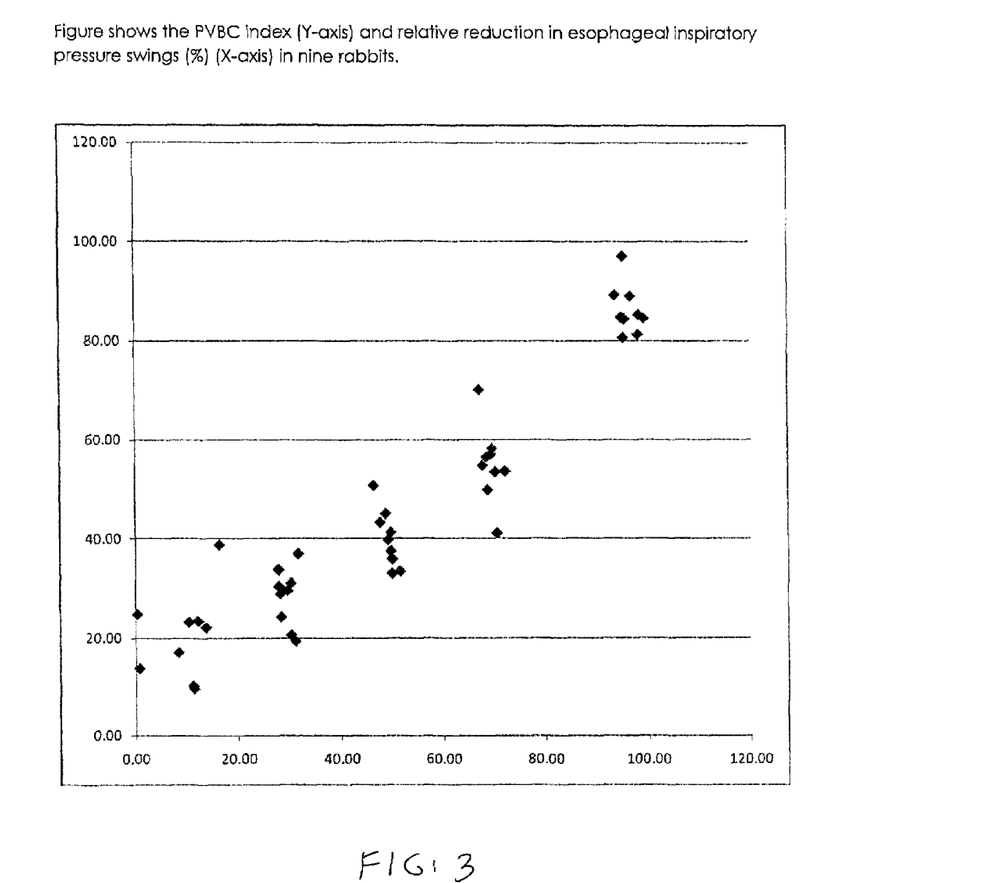
FIG. 3 is a graph of the patient-ventilator breath contribution (PVBC) index (Y-axis) "versus" a relative reduction in esophageal inspiratory pressure swings (%) (X-axis) in nine (9) rabbits.
Figure 4:
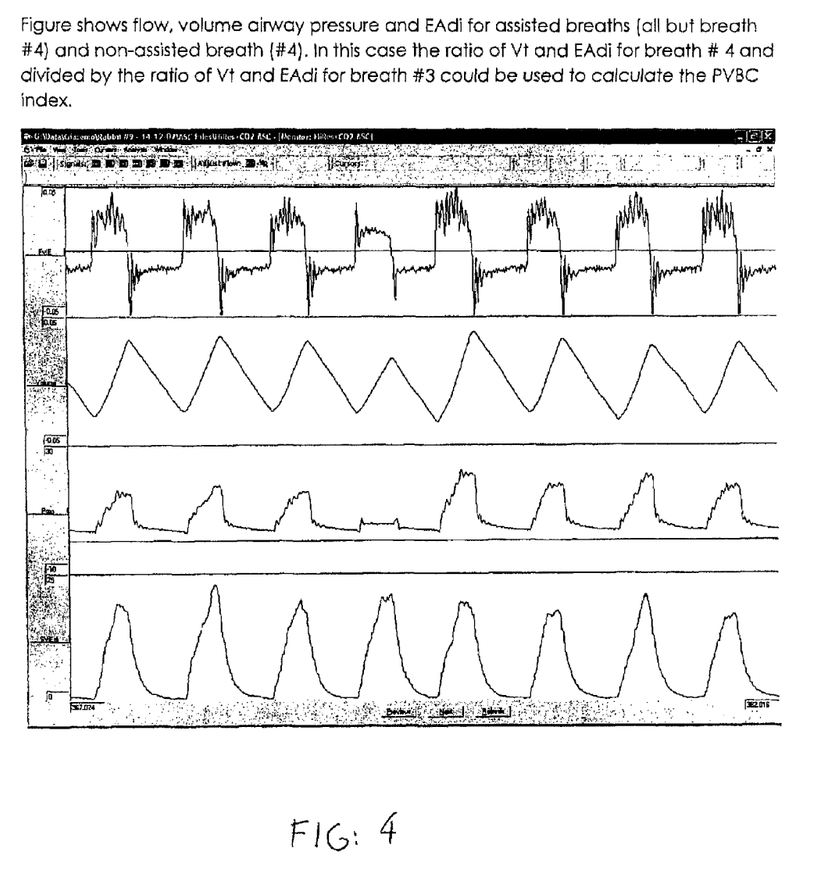
FIG. 4 show graphs of inspiratory flow, inspiratory volume, airway pressure and diaphragm electrical activity during a patient's breaths with mechanical ventilatory assist except for the fourth breath during which no mechanical ventilatory assist is applied to the patient, wherein the ratio of the inspiratory volume to the diaphragm electrical activity during the non-ventilatory-assisted fourth breath divided by the ratio of the inspiratory volume to the diaphragm electrical activity during the ventilatory-assisted third breath could be used to calculate the patient-ventilator breath contribution (PVBC) index.

This experimentation has shown that the patient-ventilator breath contribution (PVBC) index decreased with increasing ventilatory assist and was proportional to the relative reduction of inspiratory esophageal pressure deflections following a regression coefficient near one (1), with a determination coefficient which is above 0.8. Reference is made to FIGS. 3 and 4 of the appended drawings.

Although the present invention has been described in the foregoing description by means of a non-restrictive illustrative embodiment, this illustrative embodiment can be modified at will within the scope of the appended claims, without departing from the spirit and nature of the subject invention.

What is claimed is:

1. A method for determining a patient-ventilator breath contribution index in a spontaneously breathing, mechanically ventilated patient, comprising:
    measuring electrical activity of a patient's respiratory muscle during inspiration and without mechanical ventilatory assist;
    measuring a patient's inspiratory volume without mechanical ventilatory assist;
    calculating a patient's efficiency to generate an inspiratory volume without mechanical ventilatory assist as a first ratio between the inspiratory volume measured without mechanical ventilatory assist and the electrical activity of the patient's respiratory muscle measured without mechanical ventilatory assist;
    measuring electrical activity of the patient's respiratory muscle during inspiration and with mechanical ventilatory assist;
    measuring a patient's inspiratory volume with mechanical inspiratory assist;
    calculating a patient's efficiency to generate an inspiratory volume with mechanical ventilatory assist as a second ratio between the inspiratory volume measured with mechanical ventilatory assist and the electrical activity of the patient's respiratory muscle measured with mechanical ventilatory assist; and
    calculating the patient-ventilator breath contribution index as a third ratio between the calculated patient's efficiency to generate an inspiratory volume without mechanical ventilatory assist and the calculated patient's efficiency to generate an inspiratory volume with mechanical ventilatory assist.

2. A method as defined in claim 1, wherein calculating the patient's efficiency to generate an inspiratory volume without mechanical ventilatory assist comprises calculating the first ratio as a ratio of the inspiratory volume measured without mechanical ventilatory assist over the electrical activity of the patient's respiratory muscle measured without mechanical ventilatory assist.

3. A method as defined in claim 1, wherein the patient's respiratory muscle is the patient's diaphragm.

4. A method as defined in claim 1, wherein the patient's inspiratory volume is a tidal inspiratory volume.

5. A method as defined in claim 1, wherein calculating the patient's efficiency to generate an inspiratory volume with mechanical ventilatory assist comprises calculating the second ratio as a ratio of the inspiratory volume measured with mechanical ventilatory assist over the electrical activity of the patient's respiratory muscle measured with mechanical ventilatory assist.

6. A method as defined in claim 1, wherein calculating the patient-ventilator breath contribution index comprises calculating the third ratio as a ratio of the calculated patient's efficiency to generate an inspiratory volume without mechanical ventilatory assist over the calculated patient's efficiency to generate an inspiratory volume with mechanical ventilatory assist.

7. A system for determining a patient-ventilator breath contribution index in a spontaneously breathing, mechanically ventilated patient, comprising:
    a first detector of electrical activity of a patient's respiratory muscle during inspiration without mechanical ventilatory assist and with mechanical ventilatory assist;
    a second detector of a patient's inspiratory volume without mechanical ventilatory assist and with mechanical ventilatory assist; and a calculator determining:
- a patient's efficiency to generate an inspiratory volume without mechanical ventilatory assist as a first ratio between the detected patient's inspiratory volume without mechanical ventilatory assist and the detected electrical activity of the patient's respiratory muscle during inspiration and without mechanical ventilatory assist;
- a patient's efficiency to generate an inspiratory volume with mechanical ventilatory assist as a second ratio between the detected patient's inspiratory volume with mechanical ventilatory assist and the detected electrical activity of the patient's respiratory muscle during inspiration and with mechanical ventilatory assist; and
- the patient-ventilator breath contribution index as a third ratio between the calculated patient's efficiency to generate an inspiratory volume without mechanical ventilatory assist and the calculated patient's efficiency to generate an inspiratory volume with mechanical ventilatory assist.

8. A system as defined in claim 7, wherein the calculator calculates the first ratio as a ratio of the detected patient's inspiratory volume without mechanical ventilatory assist over the detected electrical activity of the patient's respiratory muscle during inspiration and without mechanical ventilatory assist.

9. A system as defined in claim 7, wherein the patient's respiratory muscle is the patient's diaphragm.

10. A system as defined in claim 9, wherein the first detector comprises an array of electrodes mounted on a free end section of a catheter for positioning at the level of the patient's diaphragm to sense signals representative of the electrical activity of the patient's diaphragm, and wherein the calculator is responsive to the signals sensed by the array of electrodes to produce a measurement of the electrical activity of the patient's diaphragm.

11. A system as defined in claim 7, wherein the patient's inspiratory volume is a tidal inspiratory volume.

12. A system as defined in claim 11, wherein the second detector comprises a detector of a patient's inspiratory flow and an integrator of the detected patient's inspiratory flow.

13. A system as defined in claim 7, wherein the calculator calculates the second ratio as a ratio of the detected patient's inspiratory volume with mechanical ventilatory assist over the detected electrical activity of the patient's respiratory muscle during inspiration and with mechanical ventilatory assist.

14. A system as defined in claim 7, wherein the calculator calculates the third ratio as a ratio of the calculated patient's efficiency to generate an inspiratory volume without mechanical ventilatory assist over the calculated patient's efficiency to generate an inspiratory volume with mechanical ventilatory assist.

* * * * *